United States Patent
Kramer et al.

[11] 3,968,229
[45] July 6, 1976

[54] ANTIMYCOTIC COMPOSITIONS

[75] Inventors: Wolfgang Krämer; Karl Heinz Büchel; Manfred Plempel, all of Wuppertal, Germany

[73] Assignee: Bayer Aktiengesellschaft, Germany

[22] Filed: June 21, 1974

[21] Appl. No.: 481,660

[30] Foreign Application Priority Data
June 30, 1973 Germany............................ 2333355

[52] U.S. Cl. .............................................. 424/273
[51] Int. Cl.² ...................................... A61K 31/415
[58] Field of Search ................................. 424/273

[56] References Cited
UNITED STATES PATENTS
3,842,097  10/1974  Tweit ................................. 424/273

*Primary Examiner*—Jerome D. Goldberg

[57] ABSTRACT

Pharmaceutical compositions are produced which comprise combining an antimycotically effective amount of a compound of the formula

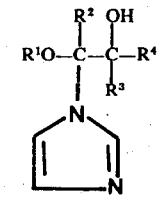

or a pharmaceutically acceptable, nontoxic salt thereof, wherein
- $R^1$ is unsubstituted or substituted aryl,
- $R^2$ is hydrogen, alkyl or unsubstituted or substituted aryl,
- $R^3$ is hydrogen, alkyl, cycloalkyl, unsubstituted or substituted aryl or unsubstituted or substituted aralkyl, and
- $R^4$ is hydrogen, alkyl, alkenyl, cycloalkyl, unsubstituted or substituted aryl, or unsubstituted or substituted aralkyl, provided that $R^3$ and $R^4$ are not both hydrogen atoms, in combination with a pharmaceutically-acceptable, nontoxic, inert diluent or carrier.

36 Claims, No Drawings

ANTIMYCOTIC COMPOSITIONS

The present invention relates to antimycotic compositions and to methods of treating mycoses in humans and animals wherein the active agent is an imidazolyl-O,N-acetal or a pharmaceutically-acceptable, nontoxic salt thereof.

More particularly, the present invention is concerned with a pharmaceutical composition which comprises an antimycotically-effective amount of a compound of the formula

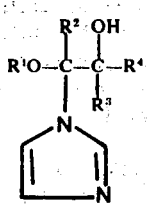

or a pharmaceutically-acceptable, nontoxic salt thereof wherein
- $R^1$ is aryl, especially of 6 to 10 carbon atoms unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy);
- $R^2$ is hydrogen, alkyl, especially lower alkyl, or aryl, especially of 6 to 10 carbon atoms unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy);
- $R^3$ is hydrogen, alkyl, especially lower alkyl, cycloalkyl, especially of 5 to 7 carbon atoms; aryl especially of 6 to 10 carbon atoms unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy); or aralkyl especially of 6 to 10 carbon atoms in the aryl moiety and 1 or 2 carbon atoms in the alkyl moiety unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy); and
- $R^4$ is hydrogen; alkyl, especially lower alkyl; alkenyl, especially lower alkenyl; cycloalkyl, especially of 5 to 7 carbon atoms; aryl, especially of 6 to 10 carbon atoms unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy); or aralkyl, especially of 6 to 10 carbon atoms in the aryl moiety and 1 to 2 carbon atoms in the alkyl moiety unsubstituted or substituted by 1 to 3 of the same or different substituents selected from the group consisting of lower alkyl, halogen, halo(lower alkyl), halo(lower alkoxy), halo(lower alkylthio), nitro, phenyl and carb(lower alkoxy);

provided that $R^3$ and $R^4$ are not both hydrogen atoms; in combination with a pharmaceutically-acceptable, nontoxic, inert diluent or carrier.

These compositions are particularly useful for their broad-spectrum antimycotic activity. The present invention also includes a method of treating mycoses in humans and animals which comprises administering to a human or animal in need thereof an antimycotically-effective amount of an imidazolyl-O,N-acetal, or pharmaceutically-effective, nontoxic salt thereof, as above defined. The present invention also includes administering the imidazolyl-O,N-acetals or pharmaceutically-acceptable, nontoxic salts thereof to humans or animals to prevent mycotic infections, as well as to treat existing infections.

When $R^2$, $R^3$ and/or $R^4$ are alkyl, they are preferably lower alkyl, and especially straight- or branched-chain alkyl moieties of 1 to 6, and especially 1 to 4, carbon atoms. Examples of such alkyl moieties are methyl, ethyl, n-propyl, i-propyl, n-butyl, i-butyl and t-butyl. A preferred alkyl moiety for $R^2$ is methyl and a preferred alkyl moiety for $R^4$ is the methyl moiety and the t-butyl moiety.

When $R^4$ is alkenyl, it is preferable a lower alkenyl moiety, especially straight- or branched-chain moieties of 2 to 6, and especially 3 to 6, carbon atoms. Preferred moieties are allyl and crotyl.

When $R^3$ and $R^4$ are cycloalkyl, they are cycloalkyl preferably of 5 to 7 carbon atoms, and especially 5 or 6 carbon atoms. Cyclopentyl and cyclohexyl are the preferred cycloalkyl moieties.

When $R^1$, $R^2$, $R^3$ and/or $R^4$ are aryl, phenyl and naphthyl are preferred, especially phenyl. When $R^3$ and $R^4$ are aralkyl, benzyl is the preferred moiety.

When the aryl and aralkyl moieties of $R^1$, $R^2$, $R^3$ and $R^4$ are substituted, it is preferred that such moieties have from 1 to 3, and especially 1 or 2, of the same or different substituents as defined above. When the substituent is an alkyl moiety, it is preferably a lower alkyl moiety, and especially a straight- or branched-chain alkyl moiety of 1 to 4 carbon atoms, for example, methyl, ethyl, n-propyl, i-propyl, n-butyl, i-butyl or t-butyl. The preferred halogen substituents are fluorine, chlorine and bromine. The preferred halo-alkyl substituents are those wherein the halogen atoms are preferably fluorine and/or chlorine, for example, trifluoromethyl. The preferred halo-alkoxy moieties are trifluoromethoxy, difluorochloromethoxy and pentafluoroethoxy. The preferred halo-alkylthio moieties are trifluoromethylthio and chlorodifluoromethylthio. When the substituent is a phenyl moiety, it is preferably in the ortho or para position. The preferred carbalkoxy groups are the carb(lower alkoxy) groups, especially those of 1 to 4 carbon atoms in the alkoxy moiety.

According to the present invention, the preferred salts are those resulting from the reaction of the imidazolyl-O,N-acetals, as above defined, with any suitable inorganic or organic acid. Preferred acids are the hydrogen halide acids, for example, hydrochloric acid, phosphoric acid, nitric acid, monofunctional and bifunctional carboxylic and hydroxycarboxylic acids, for example, acetic acid, maleic acid, succinnic acid, fumaric acid, tartaric acid, citric acid, salicylic acid, sorbic acid and lactic acid, and 1,5-naphthalene disulphonic acid. Particularly preferred salts are the hydrochlorides and the nitrates.

According to one embodiment of the present invention $R^1$ is aryl of 6 to 10 carbon atoms unsubstituted or substituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl carbalkoxy of 1 to 4 carbon atoms in the alkoxy moiety;

$R^2$ is hydrogen; alkyl of 1 to 4 carbon atoms; or aryl of 6 to 10 carbon atoms unsubstituted or substituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl and carbalkoxy of 1 to 4 carbon atoms in the alkoxy moiety;

$R^3$ is hydrogen; alkyl of 1 to 4 carbon atoms; cycloalkyl of 5 or 6 carbon atoms; aryl of 6 to 10 carbon atoms unsubstituted or substituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl and carbalkoxy of 1 to 4 carbon atoms in the alkoxy moiety; or aralkyl of 6 to 10 carbon atoms in the aryl moiety and 1 or 2 carbon atoms in the alkyl moiety unsubstituted or substituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl and carbalkoxy of 1 to 4 carbon atoms in the alkoxy moiety; and $R^4$ is hydrogen; alkyl of 1 to 4 carbon atoms, alkenyl of 3 to 6 carbon atoms; cycloalkyl of 5 or 6 carbon atoms; aryl of 6 to 10 carbon atoms unsubstituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl and carbalkoxy of 1 to 4 carbon atoms in the alkoxy moiety; or aralkyl of 6 to 10 carbon atoms in the aryl moiety and 1 or 2 carbon atoms in the alkyl moiety unsubstituted or substituted by 1 to 3 of the same or different substituents selected from the group consisting of lower alkyl, fluorine, chlorine or bromine, halo-alkyl of 1 or 2 carbon atoms in the alkyl moiety and 2 to 5 halogen atoms, halo-alkoxy of 1 or 2 carbon atoms in the alkoxy moiety and 3 to 5 halogen atoms, halo-alkylthio of 1 or 2 carbon atoms in the alkyl moiety and 2 to 5 halogen atoms, nitro, phenyl and carbalkoxy of 1 to 4 carbon atoms in the alkoxy moiety;

provided that $R^3$ and $R^4$ are not both hydrogen atoms.

According to another embodiment of the present invention $R^1$ is phenyl unsubstituted or substituted by 1, 2 or 3 substituents which are the same or different and are selected from the group consisting of chlorine, fluorine, bromine or alkyl of 1 to 4 carbon atoms;

$R^2$ is hydrogen or phenyl;

$R^3$ is hydrogen; and $R^4$ is alkyl of 1 to 4 carbon atoms.

According to another embodiment of the present invention $R^1$ is phenyl, chlorophenyl, dichlorophenyl, fluorophenyl or bromophenyl;

$R^2$ is hydrogen or phenyl;

$R^3$ is hydrogen; and $R^4$ is tert.-butyl.

According to another embodiment of the present invention $R^1$ is phenyl unsubstituted or substituted by 1, 2 or 3 substituents selected from the group consisting of chlorine, fluorine and bromine, by 1 or 2 substituents selected from the group consisting of chlorine, fluorine, bromine and alkyl of 1 to 4 carbon atoms, or by nitro or phenyl;

$R^2$ is hydrogen, alkyl of 1 or 2 carbon atoms, or phenyl;

$R^3$ is hydrogen; and $R^4$ is tert.-butyl.

According to another embodiment of the present invention $R^1$ is phenyl, chlorophenyl, fluorophenyl, bromophenyl, dichlorophenyl, chloromethylphenyl, trichlorophenyl, methylphenyl, tert.-butylphenyl, nitrophenyl or biphenyl;

$R^2$ is hydrogen, methyl or phenyl;

$R^3$ is hydrogen; and $R^4$ is tert.-butyl;

or the hydrochloride or nitrate salt thereof.

According to another embodiment of the present invention $R^1$ is phenyl unsubstituted or substituted by 1 or 2 chlorine, fluorine, bromine, iodine or alkyl of 1 to 4 carbon atoms; or by phenyl, chlorophenyl or dichlorophenyl;

$R^2$ is hydrogen or phenyl;

$R^3$ is hydrogen or methyl; and $R^4$ is tert.-butyl.

According to another embodiment of the present invention $R^1$ is phenyl, chlorophenyl, bromophenyl, fluorophenyl, iodophenyl, dichlorophenyl, tert.-butylphenyl, biphenyl, phenylchlorophenyl or phenyldichlorophenyl;

$R^2$ is hydrogen or phenyl;

$R^3$ is hydrogen or methyl; and $R^4$ is tert.-butyl.

A particularly preferred imidazolyl-O,N-acetal is 1-(2,4-dichlorophenoxy)-1-(imidazol-1-yl)-3,3- dimethyl-2-hydroxy-butane, as well as the hydrochloride salt and nitrate thereof.

The imidazolyl-O,N-acetals, as above defined, are obtainable both in the erythro form and in the threo form. These can be separated by fractional crystallization or via their tartrates. The imidazolyl-O,N-acetals are also in the form of racemates.

The erythro form and the threo form can also be separated into their optical antipodes according techniques per se known.

The imidazolyl-O,N-acetals, as above defined, may be used in any of their enantiomorphic or racemic forms.

The following compounds are representative of the imidazolyl-O,N-acetals above defined:

1-phenoxy-1-(imidazol-1-yl)-3,3-dimethyl-2-hydroxy-butane (erythro-form),
1-phenoxy-1-(imidazol-1-yl)-3,3-dimethyl-2-hydroxy-butane (threo-form),
1-phenoxy-1-(imidazol-1-yl)-3,3-dimethyl-2-hydroxy-butane (stereoisomer mixture),
1-(2'-chlorophenoxy)-1-(imidazol-1-yl)-3,3-dimethyl-2-hydroxy-butane,
1-(3'-chlorophenoxy)-1-(imidazol-1-yl)-3,3-dimethyl-2-hydroxy-butane,
1-(4'-chlorophenoxy)-1-(imidazol-1-yl)-3,3-dimethyl-2-hydroxy-butane,
1-(4'-fluorophenoxy)-1-(imidazol-1-yl)-3,3-dimethyl-2-hydroxy-butane,
1-(4'-bromophenoxy)-1-(imidazol-1-yl)-3,3-dimethyl-2-hydroxy-butane,
1-(4'-methylphenoxy)-1-(imidazol-1-yl)-3,3-dimethyl-2-hydroxy-butane,
1-(4'-t.-butylphenoxy)-1-(imidazol-1-yl)-3,3-dimethyl-2-hydroxy-butane,
1-(4'-diphenoxy)-1-(imidazol-1-yl)-3,3-dimethyl-2-hydroxy-butane,
1-(2'-diphenoxy)-1-(imidazol-1-yl)-3,3-dimethyl-2-hydroxy-butane,
1-(2',4'-dichlorophenoxy)-1-(imidazol-1-yl)-3,3-dimethyl-2-hydroxy-butane,
1-(2',4'-dichlorophenoxy)-1-(imidazol-1-yl)-3,3-dimethyl-2-hydroxy-butane hydrochloride,
1-(2'-methyl-4'-chlorophenoxy)-1-(imidazol-1-yl)-3,3-dimethyl-2-hydroxy-butane,
1-(2',4',5'-trichlorophenoxy)-1-(imidazol-1-yl)-3,3-dimethyl-2-hydroxy-butane,
1-phenyl-1-(2',4'-dichlorophenoxy)-1-(imidazol-1-yl)-3,3-dimethyl-2-hydroxy-butane,
1-methyl-1-(2',4'-dichlorophenoxy)-1-(imidazol-1-yl)-3,3-dimethyl-2-hydroxy-butane, and
1-(4'-nitrophenoxy)-1-(imidazol-1-yl)-3,3-dimethyl-2-hydroxy-butane.

The imidazolyl-O,N-acetals above described are disclosed, together with methods for the production thereof, and their use as pesticidal agents, in U.S. application Ser. No. 480,433 filed June 17, 1974 now U.S. Pat. No. 3,940,414 issued on Feb. 24, 1976.

According to said application, the imidazolyl-O,N-acetals above defined are produced by reducing imidazole derivatives of the formula

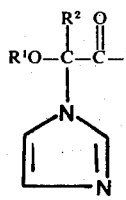

wherein $R^1$, $R^2$ and $R^4$ are as above defined, either with or without the simultaneous introduction of $R^3$, which is as above defined.

The reduction can be effected:

a. with hydrogen in the presence of a catalyst such as Raney nickel and a polar solvent, for example, methanol at 20° C to 50° C;
b. with aluminum isopropylate in the presence of an inert solvent at a temperature of from about 20° C to about 120° C, followed by hydrolysis;
c. with a complex hydride, for example, sodium borohydride or $LiAlH_4$, in the presence of a polar solvent, for example, methanol, at a temperature of from about 0° C to about 30° C, and subsequent hydrolysis, for example, with aqueous hydrochloric acid, or
d. with formamidinesulphinic acid and alkali metal hydroxide, for example, sodium hydroxide, in an aqueous solution at a temperature of from about 20° C to about 100° C in the presence of a polar solvent, for example, ethanol.

The imidazolyl-O,N-acetals can also be prepared by subjecting compounds of formula II as above defined to reductive alkylation, cycloalkylation, aralkylation or arylation by means of Grignard reagents such as alkyl-, cycloalkyl-, aralkyl- or aryl-magnesium halides, preferably the iodides or bromides; for example, with methyl-magnesium iodide in anhydrous diethyl ether at a temperature from about 20° C to about 80° C followed by hydrolysis, for example, with aqueous ammonium chloride solution.

The imidazolyl-O,N-acetals obtained may be isolated according to techniques which are per se known and may be purified, for example, by distilling off the solvent if necessary, extracting the mixture with water in a suitable organic solvent such as ethyl acetate or methylene chloride, and drying the organic phase and freeing it from the solvent. The residue thereby obtained is purified, if desired, by recrystallization or salt formation.

The salts above described are obtained according to techniques per se known, for example, by dissolving the free base in an ether, for example, diethyl ether, and adding the appropriate acid moiety, isolating the salts, for example, by filtration, and purifying, if necessary or desired.

The imidazolyl-O,N-acetals and pharmaceutically-acceptable, nontoxic salts above defined are useful as active agents in the antimycotic compositions above described and are useful in treating mycoses in humans and animals. A broad antimycotic spectrum is exhibited, especially against dermatophytes and blastomyces, as well as biphase fungi, for example, against varieties of *Candida*, such as *Candida albicans*, varieties of *Epidermophyton*, such as *Epidermophyton floccosum*, varieties of *Aspergillus*, such as *Aspergillus niger*, varieties of *Trichophyton*, such as *Trichophyton mentagrophytes*, varieties of *Microsporon*, such as *Microsporan felineum* and varieties of *Penicillium*, such as *Penicillium commune*.

Thus, the treatment of dermatomycoses and systemic mycoses caused by *Trichophyton mentagrophytes* and other species of *Trichophyton*, species of *Microsporon*, *Epidermophyton floccosum*, blastomyces and biphase fungi, as well as molds, is particularly advantageous with the compositions above described and the imidazolyl-O,N-acetals above described, as well as the pharmaceutically-acceptable, nontoxic salts thereof.

The antimycotic activity may be exemplified by the following in vitro and in vivo experimental data:

1. DETERMINATION OF THE ANTIMYCOTIC ACTIVITY IN VITRO

Description of the experiment

The nutrient substrate used was Sabourauds' milieu d'epreuve, liquid medium. The incubation temperature was 28° C and the incubation time was 24 to 96 hours. The test pathogens employed were *Candida albicans* and *Trichophyton mentagrophytes*, as well as *Aspergillus niger*, *Coccidioides immitis*, *Torulopsis glabrata* and other less important pathogens. The tests were carried out using an active compound concentration of 1.5 and 10γ/ml of nutrient medium.

The test results showed that the compounds of Examples 8, 9 and 10 complete inhibit the growth of the pathogen in concentrations greater than 5 g/ml.

2. ANTIMYCOTIC ACTION IN ANIMAL EXPERIMENTS a. Topical application in experimental trichophytosis of guinea pigs (pathogen: *Trichophyton mentagrophytes*)

Description of the experiment

A 1% strength solution of the active compounds in a dimethylsulphoxide/glycerine/water mixture (1:3:6) or in polyethylene glycol 400 was applied locally for 11 to 14 days after the trichophytosis had been produced experimentally.

Table B shows the experimental results.

Table B

| Action on *trichophytosis* of guinea pigs of the compounds of the present invention | |
|---|---|
| Compound from Example No. | Action on *Trichophyton mentagrophytes* |
| 8 | +++ |
| 10 | +++ |
| 11 | +++ |

+++ = rapid healing of the infection b. Action, when administered orally, on *Quinckeanum* trichophytosis of white mice It proved possible to suppress the development of the *Quinckeanum* infection in mice by doses of 100 mg/kg of body weight given orally twice daily up to the eighth day of infection.

The result can be seen in Table C.

Table C

| Action on *Quinckeanum trichophytosis* of white mice of the compounds of the present invention | |
|---|---|
| Compound from Example No. | Oral action on *Trichophyton quinckeanum* |
| 3 | +++ |
| 8 | +++ |
| 9 | +++ |

Table C-continued

| Action on *Quinckeanum trichophytosis* of white mice of the compounds of the present invention | |
|---|---|
| Compound from Example No. | Oral action on *Trichophyton quinckeanum* |
| 10 | +++ |

+++ = rapid healing of the infection c. Candidosis of mice

Description of the experiment

Mice of type SPF-CF$_1$ were infected intravenously with 1–2 × 10$^6$ logarithmically-growing *Candida albicans* cells suspended in physiological sodium chloride solution. One hour before the infection and seven hours after the infection, the animals were treated orally, in each case with 100 mg of the preparation/kg of body weight.

Untreated animals died of the infection 3 to 6 days after infection. The survival rate on the 6th day after infection was about 5% in the case of untreated control animals.

The experimental results are summarized in Table D.

Table D

| Action on candidoses of mice of the compounds of the present invention | |
|---|---|
| Compound from Example No. | Action on Candidosis of mice |
| 1 | ++++ |
| 3 | ++++ |
| 4 | +++++ |
| 5 | +++++ |
| 9 | +++++ |
| 10 | +++++ |

+++++ very good action = 90% surviving on 6th day after infection
++++ Good action = 80% surviving on 6th day after infection
+++ action = 60%–80% surviving on 6th day after infection The pharmaceutical compositions of the present invention contain a major or minor amount, e.g. 0.1% to 99.5%, preferably 0.5% to 95%, of active ingredient by weight of the total composition in combination with a pharmaceutically-acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form, i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage unit according to a predetermined dosage regimen, usually a whole, half, third or quarter of the daily dosage administered once, twice, three or four times a day. Other therapeutic agents can also be present.

Although the dosage and dosage regimen must in each case be carefully adjusted utilizing sound professional judgement and considering the age, weight and condition of the recipient, the route of administration and the nature and gravity of the illness, generally the dosage will be from 10 to 300, preferably from 50 to 200 mg/kg of body weight per day to achieve effective results. In some instances a sufficient therapeutic effect can be obtained at a lower dose, while in others, a larger dose will be required.

Oral administration can be effected utilizing solid and liquid dosage units forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit forms so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic, liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble solids such as polyethylene glycol, cocoa butter, higher esters as for example myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 500 mg to 30 g, preferably 2.5 g to 50 g of active agent.

While the routes of administration include oral, parenteral (i.e., intramuscular, intraperitoneal, and intravenous), rectal or topical, oral administration and topical application are particularly preferred.

The preferred pharmaceutical compositions are therefore those in a form suitable for oral administration such as tablets and suspensions and those suitable for oral administration such as tablets and suspensions and those suitable for topical application such as ointments.

Examples (a) through (d) below are illustrative of the preparation of typical pharmaceutical compositions according to the present invention:

a. 1% strength solution for topical application

Sufficient polyethylene glycol 400 is added to 1 g of the compound of Example 4, with stirring and gentle warming, to give a total of 100 g of solution.

b. 1 g of the compound of Example 4 is ground with 5 g of viscous paraffin oil. Thereafter, sufficient ointment base of paraffin oil and polyethylene is added to produce a total of 100 g of ointment.

c. Sufficient vegetable oil is added to a mixture of 10 g of the compound of Example 1, 0.05 g of sodium saccharin, 2 g of colloidal silica and 0.2 g of peppermint oil to give a total of 100 g of suspension syrup.

d. Tablets, containing 200 mg of active compound for oral administration 2 g of the compound of Example 4, 1 g of lactose and 0.3 g of cornstarch are granulated using 0.1 of cornstarch paste. The mixture is beaten through a sieve of about 4 to 6 mm mesh width and dried. This dried mixture is homogenized by passing it through a sieve of 0.8 to 1 mm mesh width and is then mixed with 0.15 g of starch and 0.02 g of magnesium stearate. The mixture thus obtained is pressed to give 10 tablets.

The following nonlimitative examples more particularly illustrate the present invention.

EXAMPLE 1

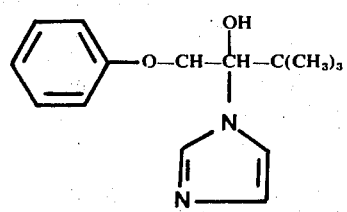

METHOD (A)

25.8 g (0.1 mol) of 1-phenoxy-1-(imidazol-1-yl)-3,3-dimethyl-butan-2-one are dissolved in 250 ml of methanol and 5.9 g (0.15 mol) of sodium borohydride are introduced in portions into this solution at 5°C to 10°C while stirring and using a reflux condenser. After stirring for 15 hours at room temperature, 20 ml of concentrated hydrochloric acid are added and the reaction mixture is stirred for a further 15 hours at room temperature and then poured into 300 ml of saturated sodium bicarbonate solution. The mixture is extracted with twice 100 ml of methylene chloride, the organic phase is washed with twice 100 ml of water and dried over sodium sulphate, and the solvent is distilled off in a water pump vacuum. The residue is triturated with 30 ml of petroleum ether.

21.6 g (83% of theory) of 1-phenoxy-1-(imidazol-1-yl)-3,3-dimethyl-2-hydroxy-butane of melting point 99°–105°C (a mixture of the erythro-form and threo-form) are obtained.

METHOD (B)

12.3 g (0.048 mol) of 1-phenoxy-1-(imidazol-1-yl)-3,3-dimethyl-butan-2-one are dissolved in 50 ml of anhydrous ether. This solution is added dropwise to a suspension of 2.6 g(0.07 mol) of lithium aluminium hydride in 80 ml of anhydrous ether and the reaction mixture is heated for 1 hour under reflux and left to stand overnight. Water is then added dropwise to the reaction mixture, while cooling with ice, in order to destroy excess lithium aluminum hydride, the mixture is then introduced into 20% strength cold sodium hydroxide solution and extracted with twice 100 ml of ether, the organic phase is dried over sodium sulphate and the solvent is distilled off in vacuo. The resulting oil is boiled up with petroleum ether and crystallises. The precipitate is filtered off hot.

1.6 g (13% of theory) or erythro-1-phenoxy-1-(imidazol-1-yl)-2-hydroxy-3,3-dimethyl-butane of melting point 125°C are obtained.

The filtrate is cooled. This again produces a precipitate which is filtered off. From this fraction, 1.4 g (11% of theory) of threo-1-phenoxy-1-(imidazol-1-yl)-2-hydroxy-3,3-dimethyl-butane of melting point 106° C to 107° C are obtained.

The compounds of Examples 2 to 12 can be obtained analogously.

Table 1

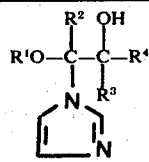

| Example No. | R¹ | R² | R³ | R⁴ | Melting Point °C |
|---|---|---|---|---|---|
| 2 | 3-Cl-C₆H₄- | H | H | C(CH₃)₃ | 116 |
| 3 | 4-Cl-C₆H₄- | H | H | C(CH₃)₃ | 145–147 |
| 4 | 4-Br-C₆H₄- | H | H | C(CH₃)₃ | 173–174 |
| 5 | 4-F-C₆H₄- | H | H | C(CH₃)₃ | 103–105 |
| 6 | 4-(CH₃)₃C-C₆H₄- | H | H | C(CH₃)₃ | 145–150 |
| 7 | 2-C₆H₅-C₆H₄- | H | H | C(CH₃)₃ | 127–129 |
| 8 | 4-C₆H₅-C₆H₄- | H | H | C(CH₃)₃ | 136–148 |

Table 1-continued

[Structure: R¹O-C(R²)(H)-C(OH)(R⁴)(-) with imidazole N-attached at R³ position]

| Example No. | R¹ | R² | R³ | R⁴ | Melting Point °C |
|---|---|---|---|---|---|
| 9 | 3,4-dichlorophenyl | H | H | $C(CH_3)_3$ | 101–109 |
| 10 | 3,4-dichlorophenyl | H | H | $C(CH_3)_3$ | Hydrochloride 190–210 |
| 11 | 2,6-dichlorophenyl | H | H | $C(CH_3)_3$ | 95–102 |
| 12 | 3,4-dichlorophenyl | phenyl | H | $C(CH_3)_3$ | 159–160 |
| 13 | 4-chlorophenyl | H | $CH_3$ | $C(CH_3)_3$ | 162–163 |
| 14 | 3-chlorobiphenyl | H | H | $C(CH_3)_3$ | 89–95 |
| 15 | 3,4-dichlorobiphenyl | H | H | $C(CH_3)_3$ | 110–113 |

Table 2

Reactants for Producing Compounds of Table 1

| Example No. | Reactants |
|---|---|
| 2 | 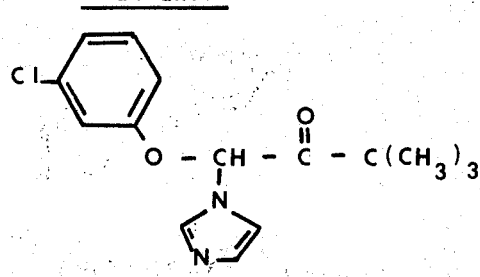 |
| 3 | 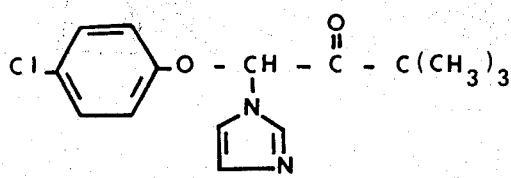 |

Table 2
Reactants for Producing Compounds of Table 1

| Example No. | Reactants |
|---|---|
| 4 | 4-Br-C$_6$H$_4$-O-CH(Im)-C(=O)-C(CH$_3$)$_3$ |
| 5 | 4-F-C$_6$H$_4$-O-CH(Im)-C(=O)-C(CH$_3$)$_3$ |
| 6 | 4-(CH$_3$)$_3$C-C$_6$H$_4$-O-CH(Im)-C(=O)-C(CH$_3$)$_3$ |
| 7 | 2-C$_6$H$_5$-C$_6$H$_4$-O-CH(Im)-C(=O)-C(CH$_3$)$_3$ |
| 8 | 4-C$_6$H$_5$-C$_6$H$_4$-O-CH(Im)-C(=O)-C(CH$_3$)$_3$ |
| 9 | 2,3-Cl$_2$-C$_6$H$_3$-O-CH(Im)-C(=O)-C(CH$_3$)$_3$ |
| 10 | 2,4-Cl$_2$-C$_6$H$_3$-O-CH(Im)-C(=O)-C(CH$_3$)$_3$ |
| 11 | 2,6-Cl$_2$-C$_6$H$_3$-O-CH(Im)-C(=O)-C(CH$_3$)$_3$ |

(Im = 1-imidazolyl attached to the CH)

Table 2

Reactants for Producing Compounds of Table 1

| Example No. | Reactants |
|---|---|
| 12 | 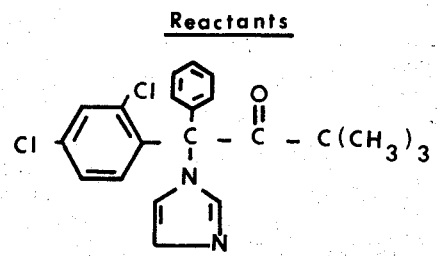 |
| 13 | 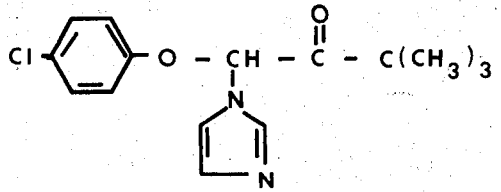 |
| 14 | 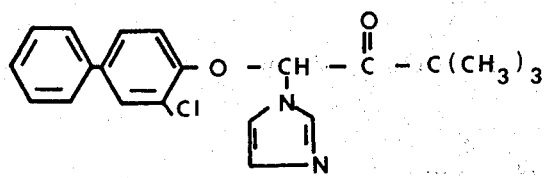 |
| 15 | 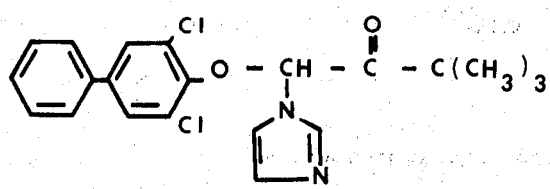 |

What is claimed:

1. A pharmaceutical composition for treating mycotic infections in humans and animals which comprises an antimycotically effective amount of a compound of the formula

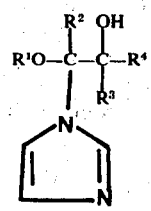

or a pharmaceutically acceptable, nontoxic salt thereof, wherein $R^1$ is phenyl substituted by 1 to 3 halogen moieties;
$R^2$ is hydrogen;
$R^3$ is hydrogen; and
$R^4$ is lower alkyl in combination with a pharmaceutically acceptable, nontoxic, inert diluent or carrier.

2. A composition according to claim 1 wherein $R^1$ is phenyl substituted by 1 to 3 of the same or different substituents selected from the group consisting of fluorine, chlorine and bromine; and $R^4$ is alkyl of 1 to 4 carbon atoms.

3. A composition according to claim 1 wherein $R^1$ is phenyl, chlorophenyl, dichlorophenyl, fluorophenyl or bromophenyl; and $R^4$ is tert.-butyl.

4. A composition according to claim 1 wherein $R^1$ is phenyl substituted by 1, 2 or 3 substituents selected from the group consisting of chlorine, fluorine and bromine; and $R^4$ is tert.-butyl.

5. A composition according to claim 1 wherein $R^1$ is phenyl, chlorophenyl, fluorophenyl, bromophenyl, dichlorophenyl, chloromethylphenyl or trichlorophenyl; and $R^4$ is tert.-butyl.

6. A composition according to claim 5 wherein the compound is in the form of the hydrochloride or the nitrate.

7. A composition according to claim 1 wherein $R^1$ is phenyl substituted by 1 or 2 chlorine, fluorine, bromine or iodine moieties; and $R^4$ is tert.-butyl.

8. A composition according to claim 1 wherein $R^1$ is phenyl, chlorophenyl, bromophenyl, fluorophenyl, iodophenyl or dichlorophenyl; and $R^4$ is tert.-butyl.

9. A pharmaceutical composition according to claim 1 in oral administration form.

10. A pharmaceutical composition according to claim 1 in topical application form.

11. A composition according to claim 1 wherein $R^1$ is

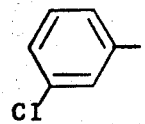

$R^2$ is hydrogen;
$R^3$ is hydrogen; and
$R^4$ is $C(CH_3)_3$.

12. A composition according to claim 1 wherein $R^1$ is

$R^2$ is hydrogen;
$R^3$ is hydrogen; and
$R^4$ is $C(CH_3)_3$.

13. A composition according to claim 1 wherein $R^1$ is

$R^2$ is hydrogen;
$R^3$ is hydrogen; and
$R^4$ is $C(CH_3)_3$.

14. A composition according to claim 1 wherein $R^1$ is

$R^2$ is hydrogen;
$R^3$ is hydrogen; and
$R^4$ is $C(CH_3)_3$.

15. A composition according to claim 1 wherein $R^1$ is

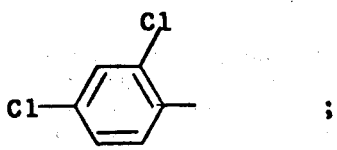

$R^2$ is hydrogen;
$R^3$ is hydrogen; and
$R^4$ is $C(CH_3)_3$.

16. A composition according to claim 1 wherein the compound is in the form of the hydrochloride salt and $R^1$ is

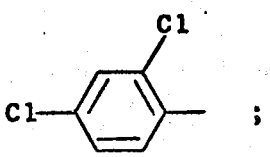

$R^2$ is hydrogen;
$R^3$ is hydrogen; and
$R^4$ is $C(CH_3)_3$.

17. A composition according to claim 1 wherein $R^1$ is

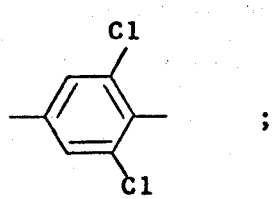

$R^2$ is hydrogen;
$R^3$ is hydrogen; and
$R^4$ is $C(CH_3)_3$.

18. A composition according to claim 1 wherein $R^1$ is

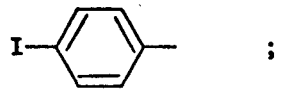

$R^2$ is hydrogen;
$R^3$ is hydrogen; and
$R^4$ is $C(CH_3)_3$.

19. A method of treating mycoses in humans and animals which comprises administering to a human or animal in need thereof an antimycotically effective amount of a compound of the formula

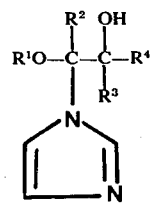

or a pharmaceutically acceptable, nontoxic salt thereof, wherein
$R^1$ is phenyl substituted by 1 to 3 halogen moieties;
$R^2$ is hydrogen;
$R^3$ is hydrogen; and
$R^4$ is lower alkyl;
in combination with a pharmaceutically acceptable, nontoxic, inert diluent or carrier.

20. A method according to claim 19 wherein
$R^1$ is phenyl substituted by 1 to 3 of the same or different substituents selected from the group consisting of fluorine, chlorine and bromine
and $R^4$ is alkyl of 1 to 4 carbon atoms.

21. A method according to claim 19 wherein
$R^1$ is phenyl, chlorophenyl, dichlorophenyl, fluorophenyl or bromophenyl; and
$R^4$ is tert.-butyl.

22. A method according to claim 19 wherein
$R^1$ is phenyl substituted by 1, 2 or 3 substituents selected from the group consisting of chlorine, fluorine and bromine; and
$R^4$ is tert.-butyl.

23. A method according to claim 19 wherein
$R^1$ is phenyl, chlorophenyl, fluorophenyl, bromophenyl, dichlorophenyl, chloromethylphenyl or trichlorophenyl; and
$R^4$ is tert.-butyl.

24. A method according to claim 23 wherein the compound is in the form of the hydrochloride or the nitrate.

25. A method according to claim 19 wherein
$R^1$ is phenyl substituted by 1 or 2 chlorine, fluorine, bromine or iodine moieties; and
$R^4$ is tert.-butyl.

26. A method according to claim 19 wherein
$R^1$ is phenyl, chlorophenyl, bromophenyl, fluorophenyl, iodophenyl or dichlorophenyl; and
$R^4$ is tert.-butyl.

27. A method according to claim 19 wherein the administration is.

28. A method according to claim 19 wherein the administration is by topical application.

29. A method according to claim 19 wherein R¹ is

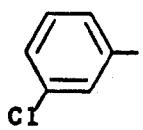

R² is hydrogen;
R³ is hydrogen; and
R⁴ is $C(CH_3)_3$.

30. A method according to claim 19 wherein R¹ is

R² is hydrogen;
R³ is hydrogen; and
R⁴ is $C(CH_3)_3$.

31. A method according to claim 19 wherein R¹ is

R² is hydrogen;
R³ is hydrogen; and
R⁴ is $C(CH_3)_3$.

32. A method according to claim 19 wherein R¹ is

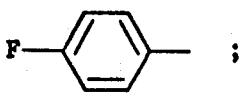

R² is hydrogen;
R³ is hydrogen; and
R⁴ is $C(CH_3)_3$.

33. A method according to claim 19 wherein R¹ is

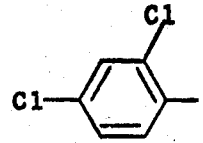

R² is hydrogen;
R³ is hydrogen; and
R⁴ is $C(CH_3)_3$.

34. A method according to claim 33 wherein the compound is in the form of the hydrochloride salt or nitrate.

35. A method according to claim 19 wherein R¹ is

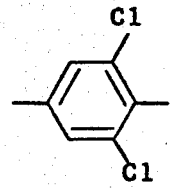

R² is hydrogen;
R³ is hydrogen; and
R⁴ is $C(CH_3)_3$.

36. A method according to claim 19 wherein R¹ is

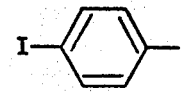

R² is hydrogen;
R³ is hydrogen; and
R⁴ is $C(CH_3)_3$.

* * * * *

UNITED STATES PATENT AND TRADEMARK OFFICE
CERTIFICATE OF CORRECTION

PATENT NO. : 3968229
DATED : July 6, 1976
INVENTOR(S) : Wolfgang Krämer; Karl Heinz Büchel; Manfred Plempel It is certified that error appears in the above-identified patent and that said Letters Patent are hereby corrected as shown below:

In claim 5, column 18, line 46, and in claim 23, column 20, line 53, delete "chloromethylphenyl".

Signed and Sealed this

Second Day of November 1976

[SEAL]

Attest:

RUTH C. MASON
Attesting Officer

C. MARSHALL DANN
Commissioner of Patents and Trademarks